United States Patent [19]

Bernstam

[11] Patent Number: 4,608,347

[45] Date of Patent: Aug. 26, 1986

[54] COMPOSITIONS, USES AND METHODS CREATING REVERSE MICELLES FOR THE CLARIFICATION OF BIOLOGICAL FLUIDS TO OBTAIN UNDISTORTED ASSAY OF ANALYTES FOLLOWING CLARIFICATION

[76] Inventor: Victor A. Bernstam, 2736 Gloucester Way, Ann Arbor, Mich. 48104

[21] Appl. No.: 368,593

[22] Filed: Apr. 15, 1982

[51] Int. Cl.[4] .......................... G01N 1/00; B01F 17/00
[52] U.S. Cl. ......................................... 436/175; 436/8; 436/17; 436/825; 252/351; 252/353; 252/355
[58] Field of Search .................... 436/8, 17, 174, 175, 436/177, 825; 252/351, 353, 355; 260/456 A

[56] References Cited

U.S. PATENT DOCUMENTS

| | | | |
|---|---|---|---|
| 4,056,468 | 11/1977 | Breiter et al. | 210/31 R |
| 4,169,074 | 9/1979 | Conrad et al. | 252/544 |
| 4,216,097 | 8/1980 | Stournas | 252/8.55 D |
| 4,239,649 | 12/1980 | Gindler et al. | 252/408 |
| 4,369,250 | 1/1983 | Gindler | 435/18 |
| 4,370,243 | 1/1983 | Chen et al. | 252/8.55 D |
| 4,372,888 | 2/1983 | Hjelmland | 260/397.1 |

OTHER PUBLICATIONS

Womack, M. D. et al, Biochimica et Biophysica Acta, vol. 733, pp. 210-215 (1983).
Penefsky, H. S. et al, Methods in Enzymology, vol. XXII, pp. 215-216 (1971).
Hjelmeland, J. M., Proc. Natl. Acad. Sci., vol. 77(11), pp. 6368-6370 (11-1980).
Bitonti, A. J. et al, Biochem. (1982), vol. 21(15), pp. 3650-3653.
Kropf, A., Vision Research, vol. 22(4), pp. 495-497 (1982).
Gonenne et al, Analytical Biochem., vol. 87, pp. 28-38 (1978).
Hjelmeland, J. M. et al, Analytical Biochem., vol. 95, pp. 201-208 (1979).
Simonds, W. F. et al, Proc. Natl. Acad. Sci., U.S.A., vol. 77, (8), pp. 4623-4627 (8-1980).
Herrmann, K. W., J. Colloid Interface Sci., vol. 22, pp. 352-359 (1966).
Hjelmeland, L. M., Chem. Abst., vol. 95, p. 376, No. 38693c(1981); vol. 94, p. 345, No. 79812p.
Snoddy, A. O. et al, Chem. Abst., vol. 74, p. 116, No. 65961m (1970).
Hirst, D. G. S. et al, Chem. Abst., vol. 75, p. 134, No. 22972u (1971).
Crabtree, P. W. et al, Chem. Abst., vol. 78, p. 91, No. 60046 (1972).

*Primary Examiner*—Thomas G. Wiseman
*Assistant Examiner*—M. Moskowitz
*Attorney, Agent, or Firm*—James M. Deimen

[57] ABSTRACT

Compositions and methods are provided for clarifying and partitioning aqueous lipid-containing specimens or samples such as lipemic serum and plasma. The compositions contain zwitterionic surfactant and water-immiscible organic solvent for lipids. The components of the compositions are selected such that they are compatible in vitro and, when constituted with aqueous specimens, do not interfere with biological or chemical activity of endogenous and exogenous analytes present in the respective specimens. The methods serve to partition the specimens into discrete aqueous and non-aqueous phases. The phases in turn can be individually assayed with respect to any of various analytes, for diagnostic or other purposes.

22 Claims, 1 Drawing Figure

COMPOSITIONS, USES AND METHODS CREATING REVERSE MICELLES FOR THE CLARIFICATION OF BIOLOGICAL FLUIDS TO OBTAIN UNDISTORTED ASSAY OF ANALYTES FOLLOWING CLARIFICATION

DESCRIPTION

1. Technical Field

The present invention is concerned with analytical or clinical chemistry. More particularly, the invention is concerned with surfactant compositions and their use in the processing or partitioning of aqueous lipid-containing specimens or samples, vegetable or animal in origin, especially biological or clinical specimens such as serum and plasma samples or other body fluids. The invention provides means for converting the specimens into discrete aqueous and non-aqueous phases, thus allowing for consequent assay of analytes (electrolytes, enzymes, blood fractions, etc.) in the separate partitioned portions of the respective samples.

2. Background Art

In a number of clinical conditions, endogenous body fluid lipid may reach high levels such that the turbidity of specimen fluid could interfere with accurate spectrophotometric determination of any of several critical analytes in the fluid. Aberrations encountered include optical perturbations and volume problems. Volume effects produced by very high concentrations of lipid may dilute the apparent concentration of electrolytes and perhaps other serum constituents, thus requiring the use of corrective equations. At present, most assay methods used in laboratories require spectrophotometric determinations of some kind. Thus, for aqueous systems, it is critical to have a reliable and efficient way to selectively eliminate lipids without introducing distortion into the determination of analytes in the particular fluid specimen.

In the case of blood, samples clarified by any of the numerous published precipitation methods such as used in the determination of cholesterol in high density lipoproteins (HDL), based on the removal of low and very low density lipoproteins (LDL and VLDL)—have been used for the assay of enzymes. However, because of the obvious distortion produced by the precipitating chemicals, there undesirably is a corresponding deleterious alteration of the levels attributed to other desired constituents that remain in the sample.

Ortega and Rodenas in Clinica Chimica Acta, Volume 92, 135–139 (1979) report on the use of phytohemagglutinins for the removal of turbidity from lipemic sera. However, this method suffers from incomplete removal of lipids. Also, information is lacking as to the reproducibility and efficiency of the method. Moreover, the method requires preliminary preparation of glutaraldehyde-treated erythrocytes saturated with *Myrtus communis L. phytohemagglutinis,* thus complicating the procedure to a point beyond the competency of the routine clinical laboratory.

Ether extraction has some limited value as a means of clarification, but as experience has shown, few severely turbid samples yield adequately to this sort of treatment, thus leaving the ultracentrifuge as a next option.

Ultracentrifugation can be used to clarify lipemic samples. However, the high cost of the equipment as well as low yield make ultracentrifugation unacceptable for many routine clinical laboratories.

For removal of lipoprotein, the use of simultaneous deionization and pH adjustment of the serum or plasma at or near the isoelectric point with the aid of anion-cation exchange resin is described in U.S. Pat. No. 4,264,471. The method provides a means for preparation of a base material or diluent for special purposes but cannot be used for assay of analytes.

Helenius and Simons in Biochemistry, Volume 10, No. 13, 2542–2547 (1971) describe the use of detergents for the removal of lipids from plasma low-density lipoproteins. However, the method is unsuitable for removal of lipids from serum. U.S. Pat. No. 4,282,001 discloses a method for reducing turbidity in samples by adding to the reaction mixture one or more detergents in organic solvents. Formulations suggested in that disclosure include buffers and salts in addition to the detergent-organic solvent adjuvant. The method is unsuitable for many purposes, however, due to dilution by the buffers, alcohols, or added salts. Moreover, the use of some detergents suggested is known to introduce optical interference and oxidizing impurities. Another drawback of the method is the limited duration of clarification, described as a maximum of 2 hours.

It is therefore an object of the present invention to provide means for overcoming the disadvantages of the prior art compositions and methods.

It is also an object of the invention to provide means in storage-stable composition form for use in clarifying aqueous lipid-containing specimens or in partitioning the same into portions that can be readily assayed.

It is another object of the invention to provide methods for removing turbidity from aqueous lipid-containing specimens, for analytical or other purposes, without resort to ultracentrifugation.

It is still another object to provide methods for assaying aqueous lipid-containing specimens without distortion, optical interference, etc.

DESCRIPTION OF THE DRAWING

These and other objects, features and advantages will be seen from the following detailed description and the accompanying drawing showing the extent of light absorption over a wavelength spectrum for comparable samples of a typical lipemic serum:
Untreated sample (curve 1),
Sample after ultracentrifugation (curve 2), and
Sample after treatment according to the present invention (curve 3).

SUMMARY AND DETAILED DESCRIPTION

Figure 1:
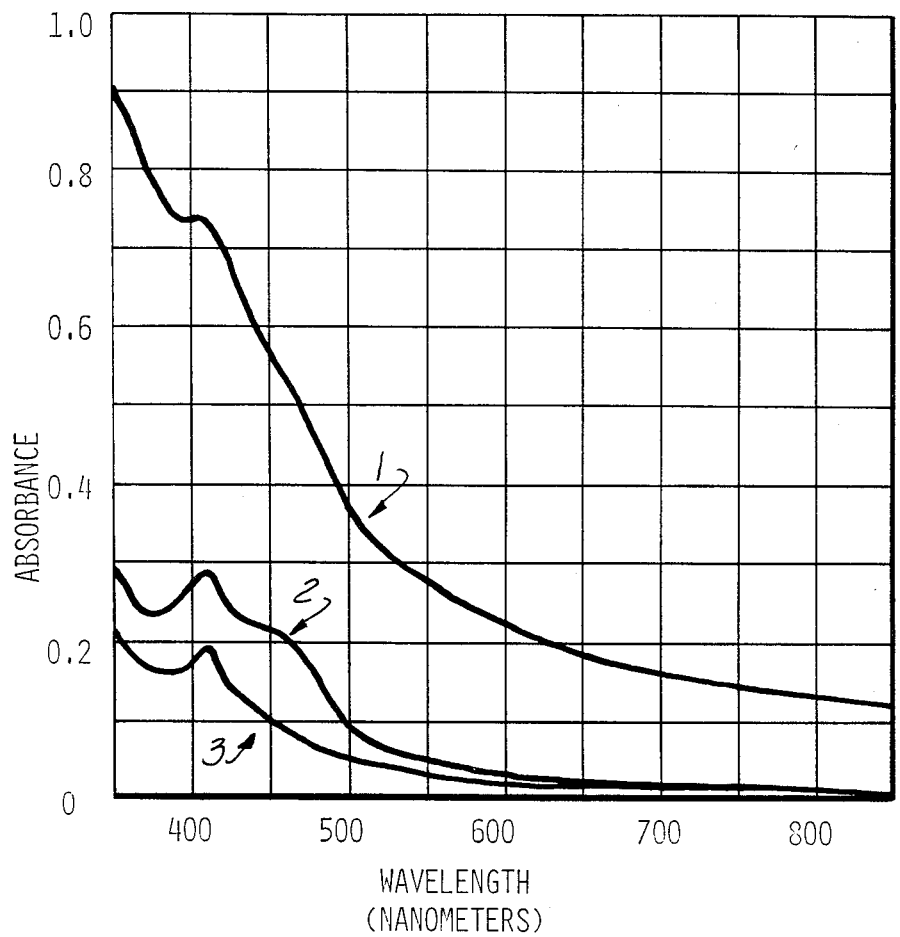

The invention in one aspect concerns surfactant compositions in storage-stable form for constituting in a mixture with an aqueous lipid-containing specimen and for partitioning the resulting mixture into an aqueous phase and a physically separate non-aqueous phase. The compositions of the invention comprise water-immiscible lipid solvent and at least one surfactant selected from 3-[$C_6$–$C_{18}$ alkyl)dimethylammonio]-1-propanesulfonates in an amount sufficient for forming lipophilic micelles in the mentioned specimen mixture, the solvent being selected such that it is compatible with the surfactant and the specimen, the solvent being sufficient in amount to dissolve the lipids present in the specimen. As a preferred option, the compositions of the invention may contain a minor, stabilizing amount of a sulfhydryl group protecting agent such as dithioerythrol and dithiothreitol (cf. Tietz, Clinical Chemistry, 2nd Edition, pp. 682–683, W. B. Saunders Co., Phila., 1976). Also, as a preferred option, the compositions of the invention may contain minor supplementary amounts of surfactants (other than the mentioned principal surfactant) compatible with the latter and the solvent, such as ionic and non-ionic surfactants.

The compositions of the invention are particularly useful for the elimination of turbidity from aqueous lipid-containing specimens. In the case of serum or plasma samples, for example, the compositions serve, when mixed with the sample, to dissociate the lipids from the other components of the sample and to accomplish the separation of the lipids from the aqueous phase into the non-aqueous phase. The mixing can be done in any suitable way as by inversion of the treated sample, vortexing, shaking, etc. The resulting aqueous phase and non-aqueous phase can be separated in any suitable way. If desired, the separation can be carried out after centrifugation (e.g., at 2,500 g.) for a brief period. Use of the compositions as described for serum or plasma typically eliminates over 95% of the triglycerides and practically all of the cholesterol. It allows for undisturbed assay of the resulting clarified aqueous phase for such constituents as electrolytes, glycose, urea, creatinine, proteins, immunoglobulins, and most enzymes. Thus, the use of an ultracentrifuge is no longer required.

The invention is applicable broadly to aqueous lipid-containing specimens and samples, especially serum, plasma and other biological fluids. For simplicity, the invention will be described herein with particular reference to blood serum and plasma as an illustrative example. The definition of serum, for example, and methods for obtaining serum specimens are well known. Detailed descriptions are available, one such being found in Clinical Diagnosis and Management by Laboratory Methods, J. B. Henry, Editor, page 53, W. B. Saunders Co., 1979, incorporated herewith by reference.

The invention is based on the finding that the instant compositions containing water-immiscible lipid solvent and dissolved surfactant as described are far superior to other detergent-solvent combinations. The latter combinations have one or more disadvantages. For example, they either removed turbidity incompletely or introduced optical interferences over the critical part of the spectrum or significantly affected assay results for many analytes such as electrolytes, proteins, glucose, and enzymes. In this regard, the absorption spectrum of wavelengths ranging from 350 to 850 nanometers is used for measuring many enzymatic activities by accepted methods. As shown in the accompanying FIGURE, the turbidity or absorbance of a lipemic serum sample treated with a composition of the invention (Curve 3) was greatly reduced as compared with that of untreated sample (Curve 1) or of untreated sample after prolonged (for over 30 minutes) ultracentrifugation (Curve 2) at accelerations of over 40,000 g.

For purposes of the invention, any of various water-immiscible lipid solvents can be employed. In general, chlorinated hydrocarbons are preferred, and for best results, one uses a low molecular weight chlorinated hydrocarbon such as chloroform. As indicated, for the surfactant one uses one or more of the 3-alkyldimethylammonio-1-propanesulfanates in which the alkyl group is a $C_6-C_{18}$ alkyl group. The surfactant is available commercially or can be made by known methods (see, for example, Analytical Biochemistry, volume 87, pages 28–39, 1978, incorporated herewith by reference). Incorporation of the surfactant into the water-immiscible lipid solvent advantageously allows not only for the disassociation of lipid from proteins but also for the formation of micelles or reversed micelles that afford protection of analytes (e.g., enzymes) against the potentially denaturing effects of organic solvents. The concentration of surfactant in the lipid solvent is not particularly critical. In general, one uses an amount that is sufficient, when the composition is constituted in the mixture with the aqueous specimen, for forming lipophilic micelles in the mixture. Preferably, one uses 1 to 3% by weight of surfactant per volume of the surfactant-solvent composition of the invention. Higher surfactant concentrations can be used but ordinarily without substantial improvement with respect to assay results or accuracy thereof. It has been established that, advantageously, the steady state distribution of the surfactant dissolved in the water-immiscible solvent (e.g., chloroform), between the aqueous phase and the non-aqueous phase, is essentially completely within the latter phase, thus leaving the clarified aqueous specimen devoid of any extraneous substance that potentially could interfere with measurement of either the true optical properties of the specimen or the analyte activity of possible interest. The compositions of the invention are clear solutions. Advantageously, they are storage-stable for prolonged periods at room temperature.

The invention in another aspect concerns methods for the removal of turbidity in aqueous lipid-containing specimens. The methods comprise constituting each such specimen in a mixture with a composition or reagent comprising water-immiscible lipid solvent and at least one surfactant selected from 3-[($C_6-C_{18}$ alkyl)-dimenthylammonio]-1-propanesulfonates in an amount sufficient for forming micelles in such mixture, and partitioning the mixture into a non-turbid aqueous phase and a physically separate non-aqueous phase. The solvent is selected such that it is compatible with the surfactant and the specimen and is sufficient in amount to dissolve the lipids present in the specimen. Suitably, the specimen (e.g., serum) is constituted with or added to the reagent composition (e.g., in a test tube) in a ratio (v/v) of about 1:2 or higher. The resulting combination is thoroughly mixed in any suitable way. This can be done conveniently by repeated inversions of the test tube or by brief (e.g., 30 seconds) mixing on a Vortex mixer. Following thorough mixing as described, the resulting discrete aqueous and and non-aqueous phases are separated in any suitable way. This can be done immediately or within a reasonable period. To facilitate the separation and completeness thereof, the specimen may be subjected to moderate centrifugation, e.g., for about 3 minutes at 2,500 g. either in the cold (e.g., at 4° C.) or at room temperature. Upon separation of the phases, the aqueous clear phase is easily removed by pipette (e.g., a Pasteur pipette) so that over 95% of the original volume of the specimen, e.g. serum specimen, can be easily recovered. The latter serum resulting from the process of the invention can be used for the assay of all the electrolytes found in untreated serum by any of the methods currently used in clinical chemistry. It also can be used for the assay of albumin, globulin, total protein, immunoglobulins, and low molecular weight substances such as $CO_2$, glucose, urea, and creatinine. Formulations containing 3% surfactant (e.g., Zwittergent ® 16, available from Calbiochem-Behring) in chloroform can be used for clarifying serum to be subsequently assayed also for various enzyme activities such as lactic dehydrogenase, creatine kinase, alkaline phosphatase, amylase, and aspartate transaminase.

According to the invention, low concentrations (e.g. 1 to 3%) of zwitterionic surfactant in chloroform can produce adequate clarification of lipemic samples with the levels of triglycerides and cholesterol often encountered in clinical laboratories. In an artificial specimen (composed of Intralipid ®, a therapeutic commercial preparation for parenteral nutrition, containing very high concentrations of triglycerides and other lipids, added to pooled normal serum to the concentration of up to 10% Intralipid) the invention proved to be effective in eliminating quantitatively all of the added lipids, thereby resulting in a clear sample.

The surfactant used in the present invention is, as indicated, commercially available. It is further so available in a graded molecular weight series. The makeup of the present surfactant compositions can be selected to achieve clarifying properties dependent upon the molecular weight of the surfactant.

The present invention provides a clarification agent and process for eliminating turbidity from lipemic serum by means of zwitterionic surfactant dissolved in water-immiscible organic solvent such as chloroform in the final concentration of about 1% to about 3% or higher. Thus, where the objective is subsequent assay of lipemic serum for low molecular weight substances such as glucose, $CO_2$, creatinine, and electrolytes (e.g., sodium, potassium, calcium, etc.) one preferably uses ammonio alkane sulfonate surfactant as specified above in which the alkyl group is a $C_{12}$–$C_{16}$ alkyl group, dissolved in chloroform at a final concentration of about 1% to about 3% or higher. Where the objective is to assay the clarified serum not only for electrolytes and low molecular weight substances but also for proteins, enzymes and immunoglobulins, a $C_{16}$-alkyl surfactant 3% in chloroform is preferred.

The method conveniently is applicable for use in any of the manual and automated methods and equipment specifically designed for clinical laboratories as well as by conventional means based on optical or electroelectronic methods used by those skilled in the art.

The invention and the best mode of practicing the same are illustrated by the following example.

EXAMPLE

A. Preparation of reagent

Zwitterionic surfactant 3-substituted ($C_{12}$-, $C_{14}$, and $C_{16}$-alkyl dimethylammonio-1-propanesulfonate, available from Calbiochem-Behring as Zwittergent ®, optionally with a minor amount of non-ionic surfactant, is dissolved in reagent grade chloroform at room temperature to provide a concentration-graded series with the final surfactant concentration of surfactant of 1 to 3% on a weight to volume basis.

B. Clarification of lipemic serum

The ratio of serum to the reagent is kept above 1:2 for optimum removal of turbidity and fast separation of the phases. Into 3.5 ml the reagent of A contained in a test tube is added 1.5 ml of serum to be clarified. The tube is not required to stand or be incubated at specific temperatures. Instead, it is immediately inverted repeatedly to mix the serum with the reagent. Alternatively, it may be mixed on the Vortex mixer for 30 seconds providing for thorough mixing of the tube content. As soon as the mixing has been obtained, the mixture is centrifuged either at room temperature or at 4° C. in a conventional laboratory centrifuge capable of attaining acceleration of 2,500 g. The mixture is centrifuged at this speed for 3–5 minutes. Longer centrifugation does not adversely affect the process. Upon completion of centrifugation, the resulting separated upper aqueous phase is removed (e.g., by Pasteur pipette) and transferred into a clean test tube. The recovery of the clarified sample is over 95%. The clarified sample thus obtained is further assayed for analytes by means which per se are conventional.

C. Examples of the effect of the invention on the electrolyte assay of normal pooled serum In a typical comparison of assay results for various analytes using the clarified serums of procedure B versus untreated serum, the following typical results were obtained:

| Analyte | Untreated Serum | Treated Serum 1% Zwittergent ® in $CHCl_3$ | | |
|---|---|---|---|---|
| | | 3-12 | 3-14 | 3-16 |
| BUN mg/dL | 17 | 19 | 18 | 19 |
| Na mmol/L | 143 | 145 | 145 | 145 |
| K mmol/L | 4.1 | 3.9 | 4.0 | 4.0 |
| CL mmol/L | 108 | 110 | 108 | 108 |
| $CO_2$ mmol/L | 20.9 | 20.7 | 20.7 | 20.8 |
| Glucose mg/dL | 99 | 95 | 96 | 98 |
| Creatinine mg/dL | 1.1 | 1.2 | 1.0 | 1.2 |

D. Examples of the effect of 3% Zwittergent ® 3-16 in chloroform on the activity of some enzymes and immunoglobulins in pooled normal plasma

| Analytes | Units | Untreated Plasma | Treated Plasma Zwittergent ® 3-16 |
|---|---|---|---|
| Creatinine kinase | U/L | 51 | 53 |
| lactate dehydrogenase | " | 61 | 62 |
| alkaline phosphatase | " | 55 | 62 |
| aspartate transaminase | " | 12 | 15 |
| amylase | " | 77 | 80 |
| albumin | g/dL | 3.9 | 4.1 |
| total protein | g/dL | 6.5 | 7.3 |
| Immunoglobulin G | mg/dL | 1090 | 1170 |
| Immunoglobulin A | " | 236 | 256 |
| Immunoglobulin M | " | 135 | 144 |

The embodiments of the invention in which an exclusive property or privilege is claimed are defined as follows:

I claim:

1. The process of creating reverse micelles for use in partitioning of aqueous lipid-containing specimens to isolate in an essentially non-denatured form water miscible analytes from said specimens comprising the steps of:

adding a composition comprising a water-immiscible organic solvent and at least one surfactant to an aqueous lipid-containing specimen containing water miscible analytes, thoroughly mixing the composition and said specimen, partitioning the mixture into a clarified aqueous phase containing said water miscible analytes and a physically separate non-aqueous organic phase containing the lipids, organic solvent, surfactants and non-polar substances extracted from the specimen and soluble in said organic solvent, and removing the separate non-aqueous organic phase from the specimen thereby removing the lipids, lipid solvent, surfactants and said non-polar substances leaving the analyte containing aqueous phase substantially free of said composition, wherein said composition comprises a water-immiscible organic solvent and at least one surfactant in the amount of at least 1% (w/v) dissolved therein selected from 3-[$C_6$–$C_{18}$ alkyl)dimethylammonio]-1-propanesulfonates, and wherein said specimen to composition ratio in the mixture is normally 1:2 (v/v) or higher to form reverse micelles in the mixture, to not dilute the concentration of any water soluble analytes originally in the specimen and to remove substantially all of the lipids present in the mixture without substantially denaturing enzymes and molecules, macromolecules and structures selected from the group consisting of genes, gene fragments, plasmids, viruses polynucleotides and nucleic acids otherwise sensitive to solvent and detergent effects.

2. The new use of the composition in claim 1 wherein the organic solvent comprises chloroform and the aqueous lipid-containing specimen comprises serum or plasma.

3. The new use of the composition in claim 1 wherein the aqueous lipid containing specimen comprises vegetable or animal body fluid.

4. The new use according to claim 1 wherein the surfactant concentration is in the range of 1% to 3% (w/v) of the composition.

5. The new use according to claim 1 wherein the surfactant is selected from the group consisting of 3-(dodecyl dimethylammonio)-1-propanesulfonate, 3-(tetradecyl dimethylammonio)-1-propanesulfonate and 3-(hexadecyl dimethylammonio)-1-propanesulfonate.

6. The new use according to claim 1 wherein the composition contains a sulfhydryl group protecting agent.

7. A method for removing turbidity in an aqueous lipid-containing specimen and separating the specimen into aqueous and non-aqueous phases without substantially denaturing labile analytes in the specimen otherwise denatured by organic solvents, the method comprising, adding the specimen to a non-aqueous composition to form a mixture, the composition comprising a water-immiscible organic solvent and at least one principal surfactant selected from 3-[($C_6$–$C_{18}$ alkyl)dimethylammonio]-1-propanesulfonates, the solvent being selected to dissolve the surfactant and to be immiscible with the specimen, said composition in the mixture in sufficient amount to form reverse micelles in the mixture and to dissolve substantially all of the lipids present in the mixture, thoroughly mixing the mixture of the composition and the specimen, partitioning the mixture into a non-turbid aqueous phase and a physically separate non-aqueous phase, said physically separate non-aqueous phase containing the lipids, lipid solvent, surfactants and other non-polar substances, and removing the physically separate non-aqueous phase thereby removing substantially all of the lipids, lipid solvent, surfactants and organic non-polar substances and thereby leaving said analyte containing aqueous phase substantially free of the composition.

8. The method according to claim 7 wherein the ratio (v/v) of specimen to composition is at least 1:2.

9. The method according to claim 7 wherein the specimen comprises vegetable or animal body fluid.

10. The method according to claim 9 wherein the fluid is serum or plasma.

11. The method according to claim 7 wherein the solvent is chloroform.

12. The method according to claim 7 wherein the composition contains at least one additional ionic or non-ionic reverse micelle forming surfactant other than the principal surfactant.

13. The method according to claim 7 wherein the composition contains a sulfhydryl group protecting agent.

14. The method according to claim 7 wherein the principal surfactant is limited to the $C_{12}$–$C_{16}$ alkyl group.

15. The method according to claim 7 wherein the principal surfactant is limited to a $C_{16}$ alkyl surfactant.

16. A non-aqueous composition for partitioning an aqueous water miscible analyte and lipid-containing specimen, the composition consisting of a water-immiscible organic solvent and at least one surfactant dissolved therein selected from the group consisting of sulfobetaine detergents consisting essentially of 3-[($C_6$–$C_{18}$ alkyl)dimethyl-ammonio]-1-propanesulfonates, as principal components and organic solvent soluble surfactants and sulfhydryl group protecting agents both as minor additional components.

17. A non-aqueous composition to prevent denaturation of water miscible analytes in a specimen by producing reverse micelles containing said analytes in a mixture of the composition and the specimen, the composition consisting of a water-immiscible organic solvent and at least one surfactant dissolved therein selected from the group of sulfobetaine detergents consisting essentially of 3-[($C_6$–$C_{18}$ alkyl)dimethyl-ammonio]-1-propanesulfonates, as principal components and organic solvent soluble surfactants capable of creating reverse micelles in non-aqueous solvents without denaturing said analytes and sulfhydryl group protecting agents both as minor additional components.

18. The composition according to claim 17 wherein the surfactant concentration is in the range of 1% to 3% (w/v).

19. The composition according to claim 17 wherein the organic solvent is chloroform.

20. The composition according to claim 17 wherein the surfactant comprises 3-(dodecyl dimethylammonio)-1-propanesulfonate.

21. The according to claim 17 wherein the surfactant comprises 3-(tetradecyl dimethylammonio)-1-propanesulfonate.

22. The composition according to claim 29 wherein the surfactant comprises 3-(hexadecyl dimethylammonio)-1-propanesulfonate.

* * * * *

UNITED STATES PATENT AND TRADEMARK OFFICE
CERTIFICATE OF CORRECTION

PATENT NO. : 4,608,347

DATED : August 26, 1986

INVENTOR(S) : Victor A. Bernstam

It is certified that error appears in the above-identified patent and that said Letters Patent are hereby corrected as shown below:

Col. 1, line 58: Correct "phytohemagglutinis" to --phytohemagglutinins--.

Col. 8, line 58: Insert -- composition -- before "according".

Col. 8, line 61: Delete "29" and substitute -- 17 --.

Signed and Sealed this

Thirty-first Day of March, 1987

Attest:

DONALD J. QUIGG

Attesting Officer

Commissioner of Patents and Trademarks